United States Patent
Mizzer et al.

(10) Patent No.: US 7,338,803 B2
(45) Date of Patent: Mar. 4, 2008

(54) METHOD FOR INCREASING CAPACITY IN AN AUTOMATIC CLINICAL ANALYZER BY USING MODULAR REAGENT DELIVERY MEANS

(75) Inventors: John Paul Mizzer, Newark, DE (US); Steven Frye, Newark, DE (US); William Jackson Devlin, Sr., Lincoln University, PA (US); Allan Tit-Shing Chow, Wilmington, DE (US)

(73) Assignee: Dade Behring Inc., Deerfield, IL (US)

( * ) Notice: Subject to any disclaimer, the term of this patent is extended or adjusted under 35 U.S.C. 154(b) by 190 days.

(21) Appl. No.: 10/623,355

(22) Filed: Jul. 18, 2003

(65) Prior Publication Data

US 2005/0014272 A1    Jan. 20, 2005

(51) Int. Cl.
*G01N 35/02* (2006.01)
(52) U.S. Cl. .............. 436/45; 422/63; 422/64; 422/67; 436/43; 436/47; 436/49; 436/54
(58) Field of Classification Search ............ 422/63–67; 436/43, 47, 49, 54, 45
See application file for complete search history.

(56) References Cited

U.S. PATENT DOCUMENTS

| | | | | |
|---|---|---|---|---|
| 3,615,239 A | * | 10/1971 | Jones et al. ............. | 422/65 |
| 3,909,201 A | * | 9/1975 | Matte ...................... | 422/65 |
| 3,985,508 A | * | 10/1976 | Williams .................. | 422/65 |
| 4,039,286 A | * | 8/1977 | Keller et al. ............. | 436/47 |
| 4,058,367 A | * | 11/1977 | Gilford .................... | 422/63 |
| 4,113,436 A | * | 9/1978 | Werder et al. ........... | 422/65 |
| 4,338,279 A | * | 7/1982 | Orimo et al. ............ | 422/64 |
| 4,459,265 A | * | 7/1984 | Berglund ................. | 422/64 |
| 4,774,055 A | * | 9/1988 | Wakatake et al. ........ | 422/64 |
| 4,906,433 A | * | 3/1990 | Minekane ................ | 422/64 |
| 4,965,049 A | * | 10/1990 | Lillig et al. ............. | 422/68.1 |
| 5,087,423 A | * | 2/1992 | Ishibashi ................. | 422/67 |
| 5,306,510 A | * | 4/1994 | Meltzer ................... | 422/65 |
| 5,352,612 A | * | 10/1994 | Huber et al. ............. | 436/47 |
| 5,434,083 A | | 7/1995 | Mitsumaki et al. | |
| 5,576,215 A | | 11/1996 | Burns et al. | |
| 5,679,309 A | * | 10/1997 | Bell ........................ | 422/67 |
| 5,762,873 A | * | 6/1998 | Fanning et al. ......... | 422/65 |
| 5,846,491 A | | 12/1998 | Choperena et al. | |
| 5,902,549 A | | 5/1999 | Mimura et al. | |
| 5,985,214 A | * | 11/1999 | Stylli et al. ............. | 422/65 |
| 5,985,672 A | | 11/1999 | Kegelman et al. | |
| 6,522,976 B2 | | 2/2003 | Shiba et al. | |
| 2003/0054557 A1 | | 3/2003 | Devlin, Sr. | |

FOREIGN PATENT DOCUMENTS

| JP | 2-173570 | * | 7/1990 |
|---|---|---|---|
| JP | 4-47267 | * | 2/1992 |

* cited by examiner

*Primary Examiner*—Arlen Soderquist
(74) *Attorney, Agent, or Firm*—Leland K. Jordan (57) ABSTRACT

An automatic clinical analyzer in which the number of cuvette ports available for reaction vessels on a reaction carousel are 50% in a configuration using a single reagent storage areas; in a second configuration an additional reagent storage areas is employed and additional ones of the cuvette ports on reaction carousel are utilized, thereby significantly increasing throughput.

4 Claims, 7 Drawing Sheets

METHOD FOR INCREASING CAPACITY IN AN AUTOMATIC CLINICAL ANALYZER BY USING MODULAR REAGENT DELIVERY MEANS

FIELD OF THE INVENTION

The present invention relates to a method and apparatus for automatically processing a patient's biological fluids such as urine, blood serum, plasma, cerebrospinal fluid and the like. In particular, the present invention provides an improved method to cost effectively increase the throughput of patient samples in a clinical analyzer adapted to perform a number of different clinical assays.

BACKGROUND OF THE INVENTION

Various types of tests related to patient diagnosis and therapy can be performed by analysis assays of a sample of a patient's infections, bodily fluids or abscesses. Such patient samples are typically placed in sample vials, extracted from the vials, combined with various reagents in special reaction vessels or tubes, incubated, and analyzed to aid in treatment of the patient. In typical clinical chemical analyses, one or two assay reagents are added at separate times to a liquid sample having a known concentration, the sample-reagent combination is mixed and incubated. Interrogating measurements, turbidimetric or fluorometric or absorption readings or the like are made to ascertain endpoint or rate values from which an amount of analyte may be determined, using well-known calibration techniques.

Although various known clinical analyzers for chemical, immunoassay and biological testing of samples are available, analytical clinical technology is challenged by increasing needs for improved operating cost efficiency. Due to increasing demands on clinical laboratories regarding assay throughput, new assays for additional analytes, accuracy of analytical results, and low reagent consumption, modern automated clinical analyzers have, by necessity, generally become larger, more complex and expensive. Clinical laboratories are therefore caught between the demand for increased functionality and the desire to minimize capital investments. In particular, the necessity for a clinical laboratory to reduce testing turnaround time is usually addressed by increasing analyzer throughput, regardless of the assay to be performed.

An important contributor to maintaining high throughput of automatic analyzers is the ability to quickly process a plurality of samples through a variety of different assay process and signal measurement steps. If no premium was placed on capital investment, increased throughput could be achieved by purchasing new analyzers to increase the rate of throughput. Such a solution is not generally acceptable to laboratory personnel and therefore new and improved clinical analyzers are needed with the capability to increase processing throughput with modest additional capital investment. Alternate approaches to this problem have been developed without directly addressing the concern for capital investment.

U.S. Pat. No. 5,434,083 uses a rotating reaction vessel train in which an analysis time of each of the test items is set to correspond to the number of times of circulation (number of cycles) of the reaction vessels on the reaction line. A reaction vessel renew device is selectively controlled for each reaction vessel in accordance with the number of cycles. Thus, a test item which requires a short reaction time is processed in a smaller number of cycles of the reaction line and a test item which requires a long reaction time is processed in a larger number of cycles.

U.S. Pat. No. 5,576,215 operates an analyzer so that the various devices used to perform assays of patient samples are operated in accordance with a schedule developed by a scheduler routine. The scheduler routine determines interval periods between operations performed by the devices on each biological sample as a function of an entered load list and schedules instrument system operations and the determined interval periods. The analyzer performs assays of the biological samples by operating the analyzer instrument systems in accordance with the developed schedule.

U.S. Pat. No. 5,846,491 increases throughput by employing an analyzer control system with means for allocating assay resources to one of a number of reaction vessels as a function of the time cycle for that vessel and transferring reaction vessels directly from one assay resource station to another according to a chronology selected from a plurality of different predetermined chronologies.

U.S. Pat. No. 5,985,672 also addresses the need for high-speed processing by employing a pre-processor for use in performing immunoassays on samples for analytes in the sample employing concentrically positioned incubating and processing carousels. A single transfer station permits reaction vessels containing sample and reagents to be moved between the carousels. The samples are separated, washed and mixed on the processing carousel and incubated on the incubating carousel thus speeding up processing throughput.

From this discussion of the art state in automated clinical analyzers, it may be seen that while has been considerable progress has been made toward increasing processing efficiency, there remains an unmet need for a clinical analyzer that is adapted to increase throughput in a simplified manner requiring minimal additional capital investment. In particular, there is an unmet need for a clinical analyzer in which throughput can be increased in response to increased demand at a relatively low level of capital investment.

SUMMARY OF THE INVENTION

The principal object of the invention is to provide an automatic clinical in which throughput can be increased by the straightforward and relatively low cost installation of additional reagent sources. The analyzer includes a rotatable assay reaction carousel for holding reaction cuvettes that is rotated stepwise in a constant direction, the stepwise rotations separated by stationary dwell times during which assay devices operate on an assay mixture contained within the reaction cuvette. A clinical analyzer like that envisioned by the present invention has an initial reagent storage areas as well as a plurality of conventional assay operation stations, such as sensors, reagent add stations, mixing stations, separation stations, and the like. The task of increasing the analyzer's throughput as the clinical laboratory's test load increases is achieved by providing the analyzer with an initial throughput level in which the capacity for conducting assays is limited by the capacity of an operational resource like a reagent resource. If and when the clinical laboratory's test load increases beyond the initial throughput level, additional throughput capacity for conducting assays is achieved by incrementally adding additional operational resource like a reagent resource so as to provide additional assay reagents.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Figure 1:
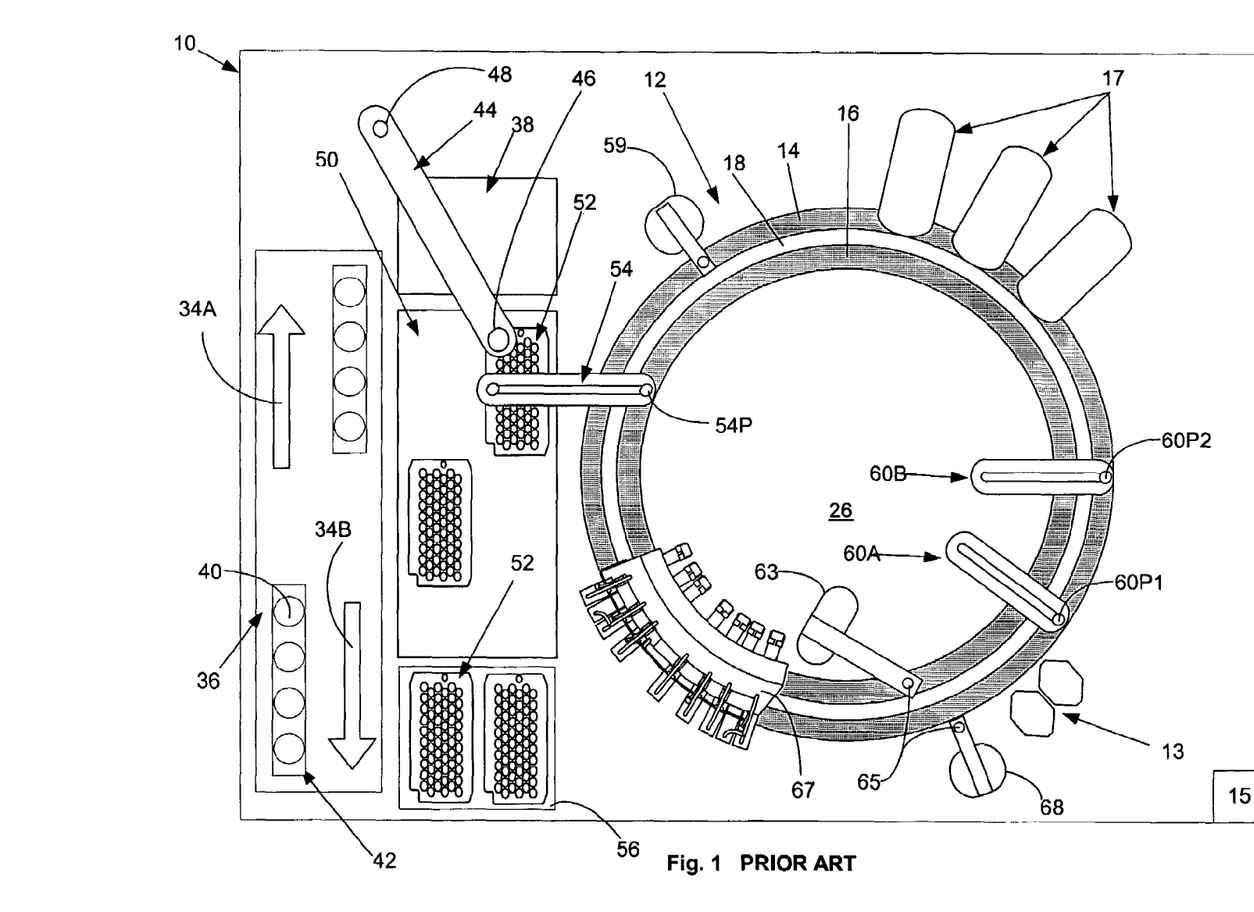
FIG. 1 is a schematic plan view of an automated analyzer in which the present invention may be employed to advantage.
Figure 2:
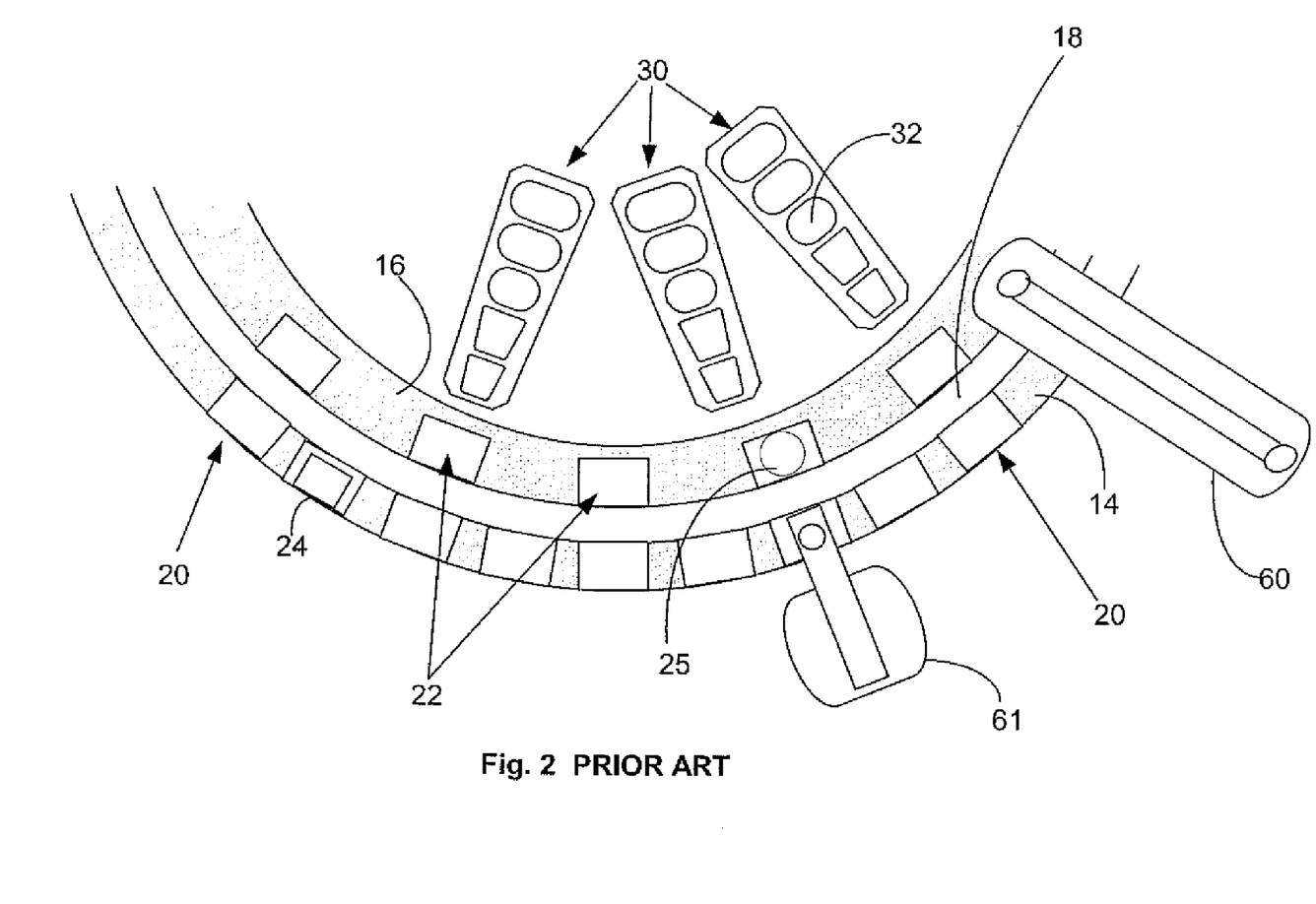
FIG. 2 is an enlarged schematic plan view of a portion of the analyzer of FIG. 1.

FIG. 1, taken with FIG. 2, shows schematically the elements of an automatic chemical analyzer 10 in which the present invention may be advantageously practiced, analyzer 10 comprising a reaction carousel 12 supporting an outer cuvette carousel 14 having cuvette ports 20 formed therein and an inner cuvette carousel 16 having vessel ports 22 formed therein, the outer cuvette carousel 14 and inner cuvette carousel 16 being separated by a open groove 18. Cuvette ports 20 are adapted to receive a plurality of reaction cuvettes 24 like disclosed in co-pending application Ser. No. 10/623,436 assigned to the assignee of the present invention and containing various reagents and sample liquids for conventional clinical and immunoassay assays while vessel ports 22 are adapted to receive a plurality of reaction vessels 25 that contain specialized reagents for ultra-high sensitivity luminescent immunoassays. Reaction carousel 12 is rotatable using stepwise movements in a constant direction, the stepwise movements being separated by a constant dwell time during which carousel 12 is maintained stationary and computer controlled assay operational devices 13, such as sensors, reagent add stations, mixing stations and the like, operate as needed on an assay mixture contained within cuvettes 24 and reaction vessels 25.

Analyzer 10 is controlled by software executed by the computer 15 based on computer programs written in a machine language like that used on the Dimension® clinical chemistry analyzer sold by Dade Behring Inc, of Deerfield, Ill., and widely used by those skilled in the art of computer-based electromechanical control programming. Computer 15 also executes application software programs for performing assays conducted by various analyzing means 17 within analyzer 10.

Temperature-controlled reagent storage area 26 stores a plurality of multi-compartment elongate reagent cartridges 30 like that described in co-pending application Ser. No. 09/949,132 assigned to the assignee of the present invention, and containing reagents in wells 32 as necessary to perform a given assay.

A bi-directional incoming and outgoing sample tube transport system 36 having input lane 34A and output lane 34B transports incoming individual sample tubes 40 containing liquid specimens to be tested and mounted in sample tube racks 42 into the sampling arc of a liquid sampling arm 44. Liquid specimens contained in sample tubes 40 are identified by reading bar coded indicia placed thereon using a conventional bar code reader to determine, among other items, a patient's identity, the tests to be performed, if a sample aliquot is to be retained within analyzer 10 and if so, for what period of time. It is also common practice to place bar coded indicia on sample tube racks 42 and employ a large number of bar code readers installed throughout analyzer 10 to ascertain, control and track the location of sample tubes 40 and sample tube racks 42.

Figure 3:
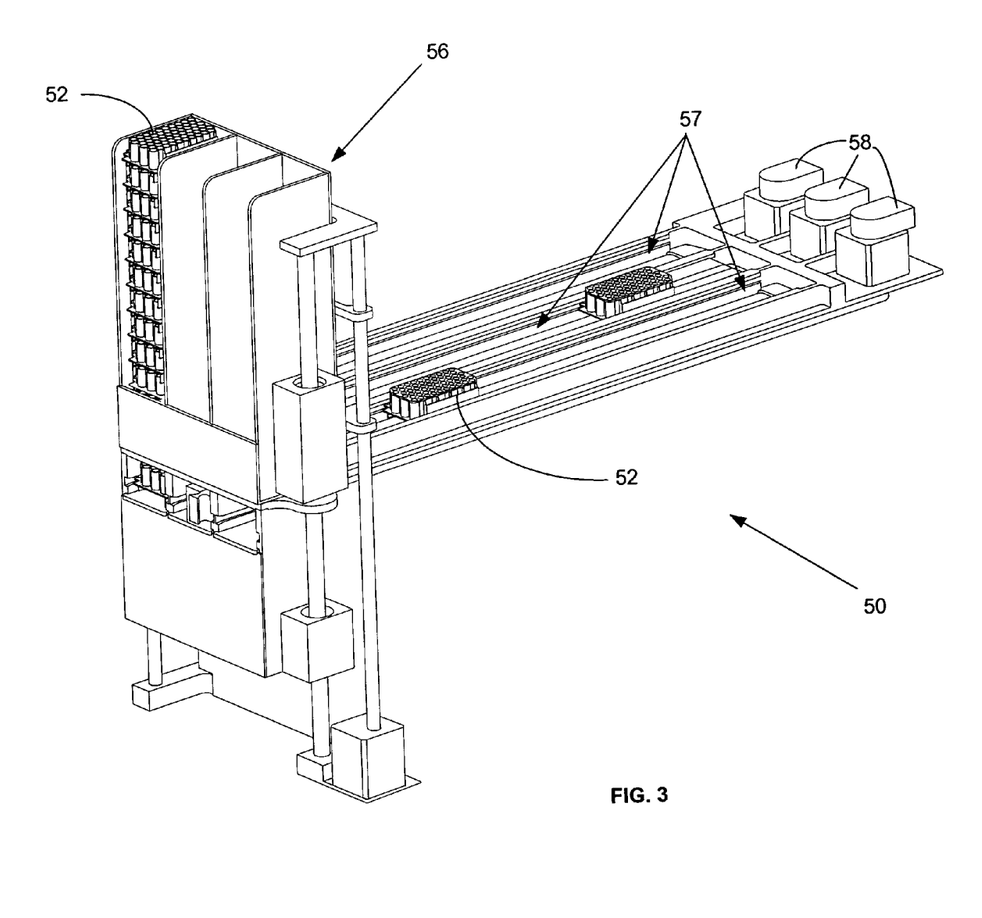
FIG. 3 is a perspective elevation view of an automated aliquot vessel array storage and handling unit.
Figure 4:
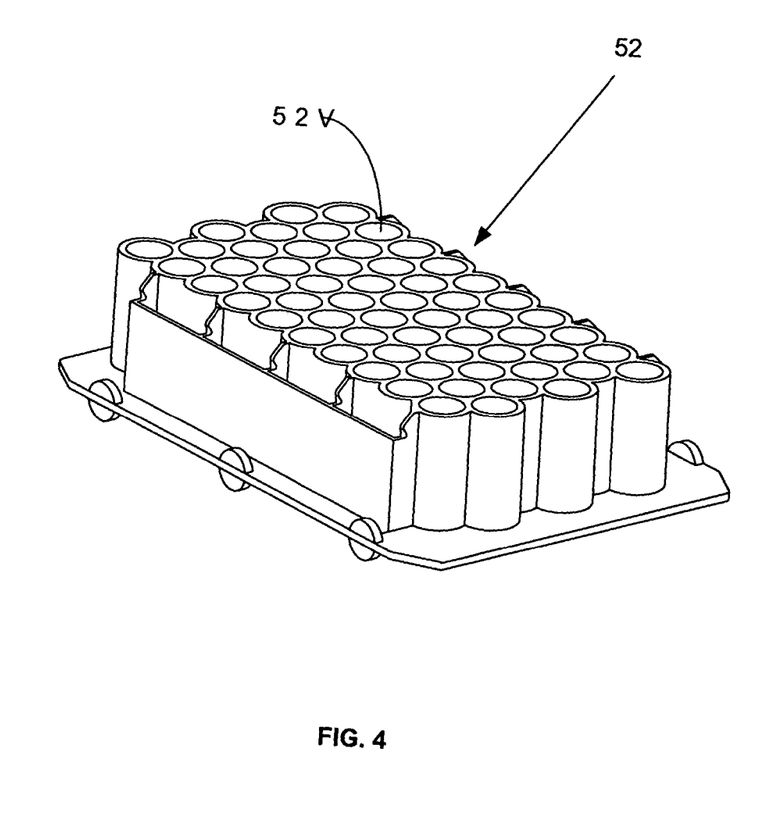
FIG. 4 is a perspective elevation view of an aliquot vessel array.

Sampling arm 44 supports a liquid sampling probe 46 mounted to a rotatable shaft 48 so that movement of sampling arm 44 describes an arc intersecting the sample tube transport system 36 and an aliquot vessel array transport system 50, as seen in FIG. 3. Sampling arm 44 is operable to aspirate liquid sample from sample tubes 40 and to dispense an aliquot sample into one or more of a plurality of vessels 52V in aliquot vessel array 52, as seen in FIG. 4, depending on the quantity of sample required to perform the requisite assays and to provide for a sample aliquot to be retained by analyzer 10 within environmental chamber 38. It is important in the present teaching that analyzer 10 be originally designed and configured so that space and other assay operational devices are also initially adapted to accommodate the addition of throughput limiting resources. For example, sample tube transport system 36 like seen in FIG. 5 is initially adapted to accommodate the addition of throughput limiting resources.

Aliquot vessel array transport system 50 comprises an aliquot vessel array storage and dispense module 56 and a number of linear drive motors 58 adapted to bi-directionally translate aliquot vessel arrays 52 within a number of aliquot vessel array tracks 57 below a sample aspiration and dispense arm 54 located proximate reaction carousel 12. Sample aspiration and dispense arm 54 is controlled by computer 15 and is adapted to aspirate a controlled amount of sample from individual vessels 52V positioned at a sampling location within a track 57 using a conventional liquid probe 54P and then liquid probe 54P is shuttled to a dispensing location where an appropriate amount of aspirated sample is dispensed into one or more cuvettes 24 in cuvette ports 20 for testing by analyzer 10 for one or more analytes. After sample has been dispensed into reaction cuvettes 24, conventional transfer means move aliquot vessel arrays 52 as required between aliquot vessel array transport system 50, environmental chamber 38 and a disposal area, not shown.

Reaction cuvette load station 68 and reaction vessel load station 63 are respectively positioned proximate outer cuvette carousel 14 and inner vessel carousel 16 and are adapted to load reaction cuvettes 24 into cuvette ports 20 sideways as described later and reaction vessels 25 into vessel ports 22 using for example a translatable robotic arm 65. In operation, used cuvettes 24 in which an assay has been finally conducted, are washed and dried in a wash station 67 like disclosed in co-pending application Ser. No. 10/623,360 assigned to the assignee of the present invention. Subsequent assays are conducted in cleaned used cuvettes 24 unless dictated otherwise for reasons like disclosed in co-pending application Ser. No. 10/318,804 assigned to the assignee of the present invention. Cuvette unload station 59 is adapted to remove unusable reaction cuvettes 24 from cuvette ports 20 again using a translatable robotic arm 65 like seen on load stations 68 and 63.

Figure 5:
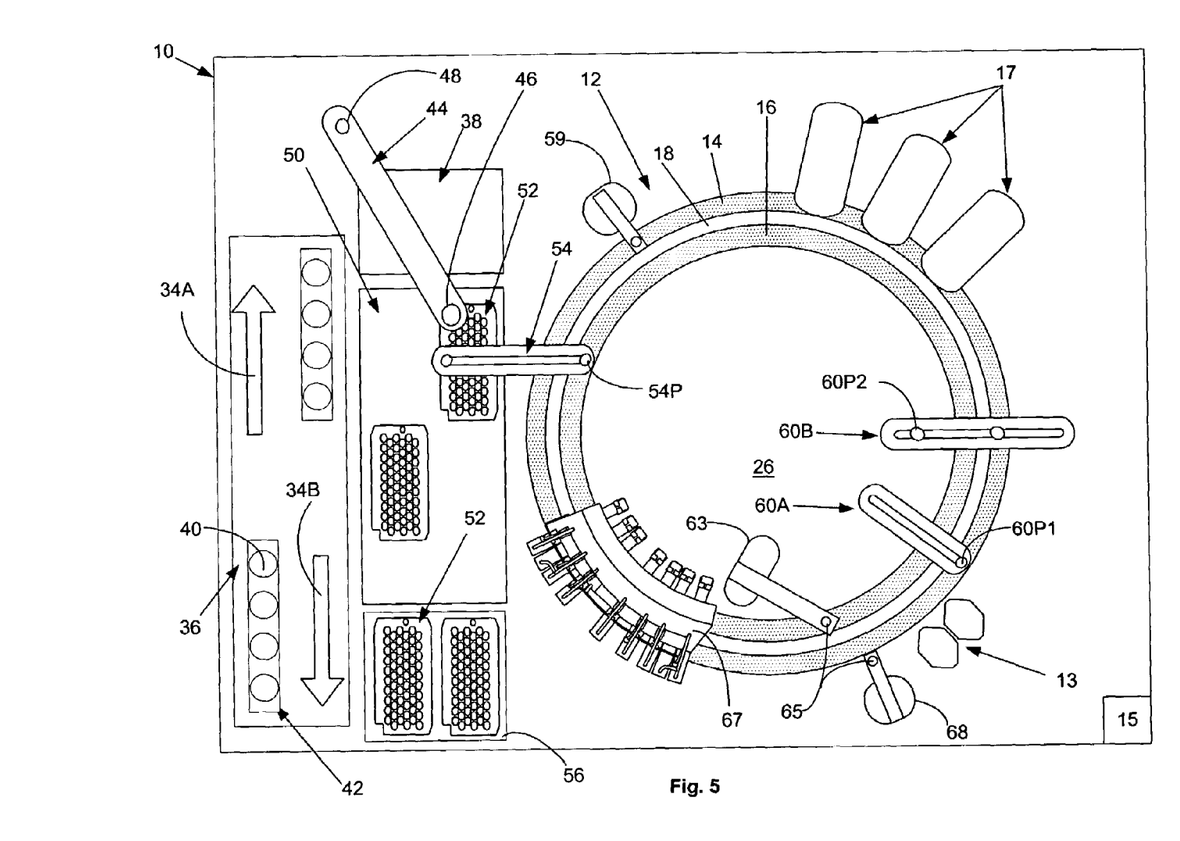
FIG. 5 is a schematic plan view of an automated analyzer in which the present invention may be employed to advantage.

As seen in FIG. 5, analyzer 10 has a first reagent aspiration and dispense arm 60A with a first moveable conventional liquid reagent probe, 60P1, mounted thereon and translatable between reagent storage area 26 and cuvette ports 20, and a second reagent aspiration and dispense arm 60B with a second moveable conventional liquid reagent probe, 60P2, mounted thereon and translatable between reagent storage area 26 and cuvette ports 20. Probes 60P1 and 60P2 comprise conventional mechanisms for aspirating reagents required to conduct specified assays from wells 32 in an appropriate reagent cartridges 30, probes 60P1 and 60P2 subsequently being translated to a reagent dispensing location where reagent(s) are dispensed into reaction cuvettes 24 in cuvette ports 20. A number of reagent cartridges 30 are inventoried in controlled environmental conditions inside reagent storage area 26.

The present invention is based on the discovery that analyzer 10 may be initially configured so that whatever operating resources are throughput limiting, those resources are adapted to be incrementally added, for example in a modular fashion, to analyzer 10 as the incoming assay demand increases. Importantly, analyzer 10 is also initially configured such that the operating resources which are not throughput limiting are also initially adapted to accommodate the addition of throughput limiting resources. The throughput of analyzer 10 as seen in FIG. 5 is directly proportional to the number of independently operated reagent storage areas like reagent storage area 26. In particular, the throughput of analyzer 10 may be expressed as:

$$T = \frac{F \times N}{A};$$

in which,

T=Throughput (in assays per unit time) of assays analyzer 10 can complete in a unit of time, F=Frequency at which probe 60P can access reagent in a cartridge 34, N=Number of independent reagent storage areas like reagent storage area 26, and A=Average number of reagent additions per assay.

This relationship may be illustrated by considering an exemplary embodiment of the present invention in which reaction carousel 12 has cuvette ports 20 rotated in a clock-wise direction using stepwise 1.5 second movements separated by a 2.1 second dwell time during which reagent probe 60P1 may aspirate reagent from a cartridge 30 while probe 60P2 is dispensing reagent into a cuvette 24 and/or being cleaned in a washing well (not shown). In such an embodiment, reaction carousel 12 is dimensioned so as to have 184 cuvettes 24 located in cuvette ports 20 in outer cuvette carousel 14. Table 1 shows the resulting throughput for analyzer 10 in this configuration in which analyzer 10 is equipped with the reagents required to perform assays having as many as 3 different reagents.

TABLE 1

| Number of Reagents Required | Reagent Aspirate and Dispense Rate of Storage Area 26 | Throughput (assays/hour) |
| --- | --- | --- |
| 1 | 1000/hour | 1000/hour |
| 2 | 1000/hour | 500/hour |
| 3 | 1000/hour | 333/hour |

Figure 6:
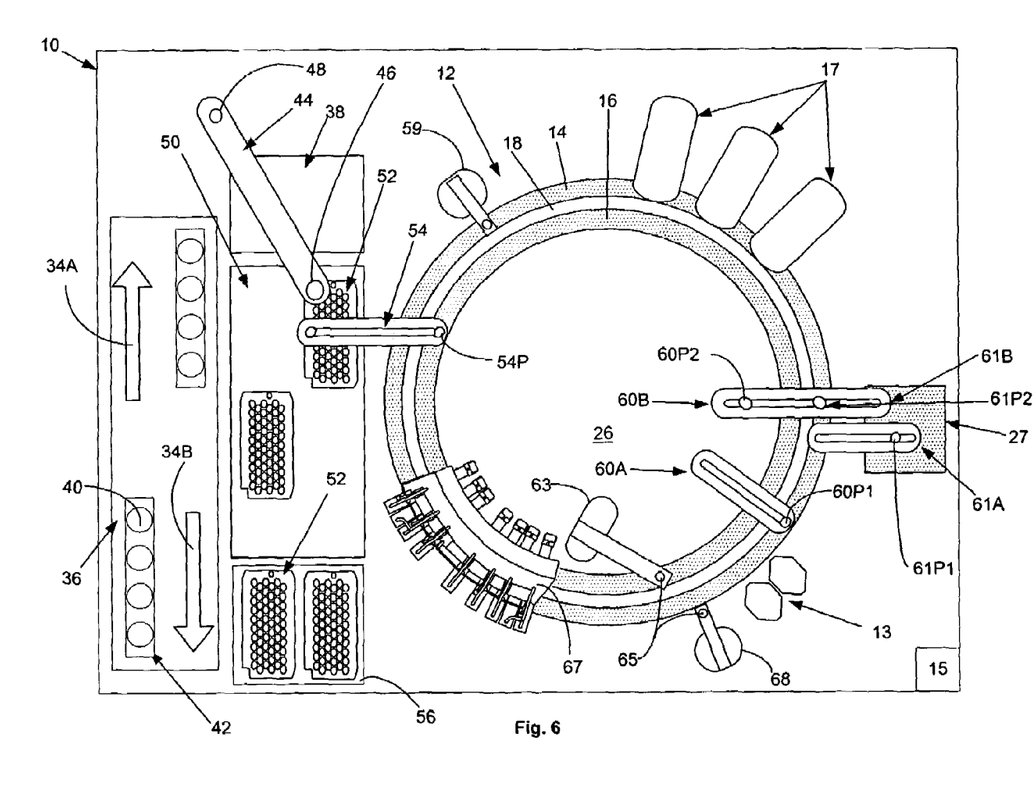
FIG. 6 is a schematic plan view of the analyzer of FIG. 1 provided with a first additional reagent resource.

A key feature of the present invention is the discovery that the throughput of analyzer 10 may be essentially doubled by adding only an additional reagent storage area 27 operating independently from the existing reagent storage area 26, while at the same time, the useage of cuvette ports 20 available for reaction vessels 24 is also increased. This is an example of how analyzer 10 is initially configured such that the operating resources which are not throughput limiting are also initially adapted to accommodate the addition of throughput limiting resources. Clearly, addition reagent aspiration and dispense arms 61A and 61B similar to arms 60A and 60B described above are also installed so as to transfer reagents between reagent storage area 27 and cuvette ports 20. This significant increase throughput of analyzer 10 by adding additional reagent storage area 27 and associated probes as shown in FIG. 6 and Table 2. In FIG. 6, aspiration and dispense arms 60B and 61B are shown as sharing a common translation mechanism for probes 60P2 and 61P2 for purposes of efficiency. This method of increasing the throughput of analyzer 10 is an important cost savings to an expanding clinical laboratory because the only additional expense is that associated with the additional reagent storage area 27 and its probes 61P1 and 61P2 as seen in FIG. 6. It may be estimated that the expense of installing reagent storage area 27 and its probes 61P1 and 61P2 is less than 10% of the original expense of analyzer 10.

TABLE 2

| Number of Reagents Required | Reagent Aspirate and Dispense Rate of Storage Area 26 | Reagent Aspirate and Dispense Rate of Storage Area 27 | Throughput (assays/hour) |
| --- | --- | --- | --- |
| 1 | 1000/hour | 1000/hour | 2000/hour |
| 2 | 1000/hour | 1000/hour | 1000/hour |
| 3 | 1000/hour | 1000/hour | 667/hour |

Figure 7:
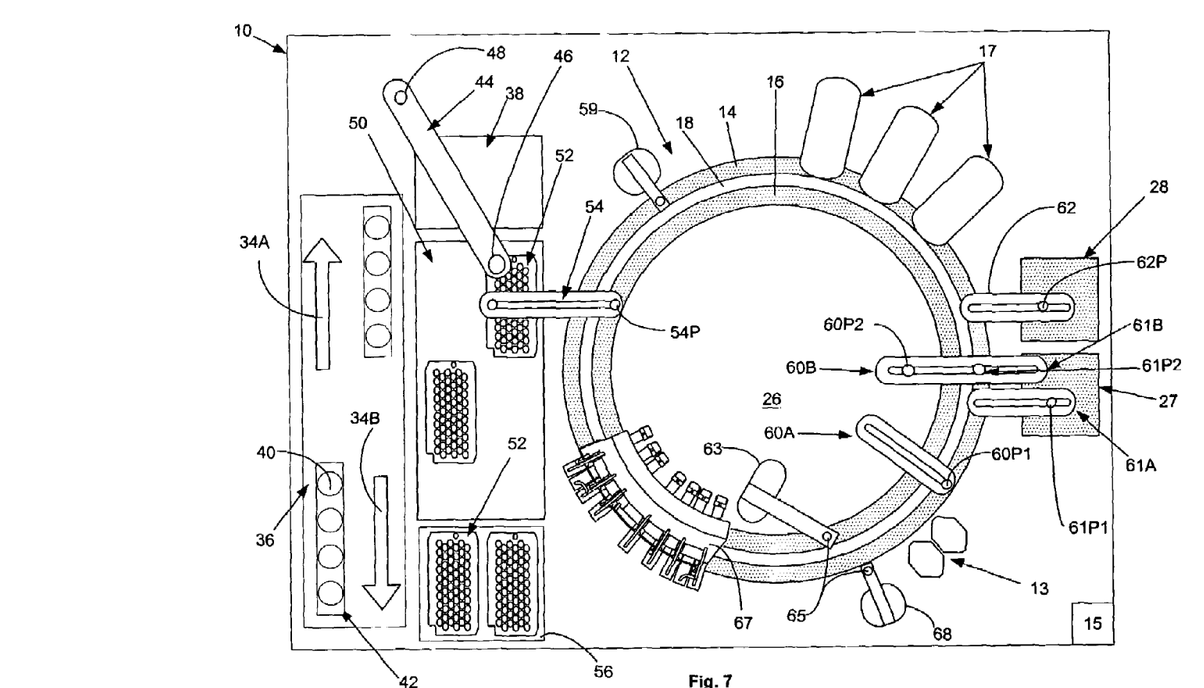
FIG. 7 is a schematic plan view of the analyzer of FIG. 1 provided with a second additional reagent resource.

An even further increase in the throughput of analyzer 10 may be achieved by the addition of a third reagent storage area 28 as seen in FIG. 7 and operating independently from the two existing reagent storage areas 26 and 27, again increasing usage of cuvette ports 20 available for reaction vessels 24. This further increase in throughput of analyzer 10 by adding additional reagent storage area 28 and at least one reagent aspiration and dispense arm 62 with probe 62P similar to arms 60A and 60B described above are also installed transfer reagents between reagent storage area 28 and cuvette ports 20. This method of increasing the throughput of analyzer 10 by initially configuring analyzer 10 such that the full number of available cuvette ports 20 is underutilized and then increasing the throughput of analyzer 10 with modular resource additions as the incoming assay demand increases is cost-effectively advantageous to an expanding clinical laboratory. The particular embodiment described here is illustrative of the more general teaching of the present invention in that clinical analyzer 10 may be initially configured so that whatever operating resources are throughput limiting, those resources are adapted to be incrementally added, for example in a modular fashion, to analyzer 10 as the incoming assay demand increases. It is important in such teaching that analyzer 10 be originally designed and configured so that space and other assay operational devices, for instance incoming and outgoing sample tube transport system 36 like seen in FIG. 5, are also initially adapted to accommodate the addition of throughput limiting resources. This is an example of how analyzer 10 is initially configured such that the operating resources which are not throughput limiting are also initially adapted to accommodate the addition of throughput limiting resources.

TABLE 3

| Number of Reagents Required | Reagent Aspirate and Dispense Rate of Storage Area 26 | Reagent Aspirate and Dispense Rate of Storage Area 27 | Reagent Aspirate and Dispense Rate of Storage Area 28 | Throughput (assays per hour) |
|---|---|---|---|---|
| 1 | 1000/hour | 1000/hour | 1000/hour | 3000/hour |
| 2 | 1000/hour | 1000/hour | 1000/hour | 1500/hour |
| 3 | 1000/hour | 1000/hour | 1000/hour | 1000/hour |

It is obvious to one skilled in the art that the above described method for operating a clinical analyzer so as to simultaneously increase throughput with an initial throughput level in which the capacity for conducting assays is limited only by the capacity of its reagent servers. If and when the clinical laboratory's test load increases beyond the initial throughput level, additional capacity for conducting assays is achieved by adding another reagent storage areas so as to provide additional assay reagents. For these reasons, the present invention is not limited to those embodiments precisely shown and described in the specification but only by the following claims.

We claim:

1. A method for increasing the assay throughput of a clinical analyzer by:
    initially configuring the analyzer with reagent resources to conduct a group of assays, said reagent resources being throughput limiting;
    initially configuring the analyzer with all other assay resources required to conduct said group of assays, said all other assay resources being not throughput limiting; and,
    incrementally adding reagent resources to the analyzer in order to increase throughput as the number of assays within said group of assays to be conducted increases.

2. The method of claim 1 wherein said additional assay reagent resources may be added to the analyzer in a first increment such that the initial assay throughput is increased by about 50%.

3. The method of claim 1 wherein said additional assay reagent resources may be added to the analyzer in first and second increments such that assay throughput is increased by about 50% and by about 33%, respectively.

4. The method of claim 1 wherein said additional assay reagent resources comprise a reagent storage area and at least one reagent aspiration and dispense arm.

* * * * *

UNITED STATES PATENT AND TRADEMARK OFFICE
CERTIFICATE OF CORRECTION

PATENT NO.         : 7,338,803 B2
APPLICATION NO. : 10/623355
DATED                 : March 4, 2008
INVENTOR(S)       : John Paul Mizzer et al.

It is certified that error appears in the above-identified patent and that said Letters Patent is hereby corrected as shown below:

1. On the title page, in the left hand column, in the inventors section (75); please delete "Steven" and insert -- Stephen --.

Signed and Sealed this

Seventeenth Day of February, 2009

JOHN DOLL
*Acting Director of the United States Patent and Trademark Office*